(12) United States Patent
Learmonth et al.

(10) Patent No.: US 8,991,697 B2
(45) Date of Patent: Mar. 31, 2015

(54) SYSTEM FOR VERIFYING AN ITEM IN A PACKAGE

(71) Applicant: TruTag Technologies, Inc., Honolulu, HI (US)

(72) Inventors: Timothy Learmonth, Oakland, CA (US); Michael P. O'Neill, Kaneohe, HI (US); Peter Pearson, Aptos, CA (US); Ting Zhou, Orinda, CA (US)

(73) Assignee: TruTag Technologies, Inc., Kapolei, HI (US)

( * ) Notice: Subject to any disclaimer, the term of this patent is extended or adjusted under 35 U.S.C. 154(b) by 0 days.

(21) Appl. No.: 14/067,747

(22) Filed: Oct. 30, 2013

(65) Prior Publication Data
US 2014/0124398 A1 May 8, 2014

Related U.S. Application Data

(62) Division of application No. 13/158,249, filed on Jun. 10, 2011, now Pat. No. 8,596,546.

(60) Provisional application No. 61/354,633, filed on Jun. 14, 2010.

(51) Int. Cl.
G06K 7/00 (2006.01)
B65D 79/02 (2006.01)
G01N 21/3563 (2014.01)
G06Q 10/08 (2012.01)

(52) U.S. Cl.
CPC ............ B65D 79/02 (2013.01); G01N 21/3563 (2013.01); G06Q 10/08 (2013.01)
USPC ........... 235/380; 235/375; 235/435; 235/439; 235/487; 235/492

(58) Field of Classification Search
USPC ................................. 235/375, 380, 487, 492
See application file for complete search history.

(56) References Cited

U.S. PATENT DOCUMENTS

| 6,771,369 | B2 | 8/2004 | Rzasa et al. | |
|---|---|---|---|---|
| 7,173,530 | B2 | 2/2007 | Lambright et al. | |
| 8,555,605 | B2 | 10/2013 | Schmitz | |
| 2007/0055470 | A1* | 3/2007 | Pietrzyk et al. | 702/104 |
| 2007/0219916 | A1 | 9/2007 | Lucas | |
| 2008/0240654 | A1* | 10/2008 | Pearson et al. | 385/37 |

FOREIGN PATENT DOCUMENTS

| JP | 2003054105 | 2/2003 |
|---|---|---|
| JP | 2005216453 | 8/2005 |
| JP | 2008279060 | 11/2008 |
| WO | 2009147874 | 12/2009 |

* cited by examiner

Primary Examiner — Matthew Mikels
(74) Attorney, Agent, or Firm — Van Pelt, Yi & James LLP

(57) ABSTRACT

A system verifying an item in a package comprises a package producer and a verifier. The package producer produces a package with a label, wherein the package includes an item each with one or more selected tag identifiers that are placed in a location on the item. The verifier verifies the item using 1) the one or more selected tag identifiers as detected using a spectral measurement or 2) a location or a shape of the one or more selected tag identifiers on the item, and 3) the label as read using a label reader.

16 Claims, 5 Drawing Sheets

SYSTEM FOR VERIFYING AN ITEM IN A PACKAGE

CROSS REFERENCE TO OTHER APPLICATIONS

This application is a divisional of co-pending U.S. patent application Ser. No. 13/158,249, entitled SYSTEM FOR VERIFYING AN ITEM IN A PACKAGE filed Jun. 10, 2011 which is incorporated herein by reference for all purposes, which claims priority to U.S. Provisional Application No. 61/354,633, entitled SYSTEM FOR VERIFYING AN ITEM IN A PACKAGE filed Jun. 14, 2010 which is incorporated herein by reference for all purposes.

BACKGROUND OF THE INVENTION

A producer or reseller of items (including ingredients and components of such items)—for example a manufacturer, but also including other parties in the entire supply and distribution chain such as a supplier, a wholesaler, a distributor, a repackager, and a retailer—especially, but not limited to, high-value items, faces counterfeiting of the item. Counterfeiting includes the substitution, dilution, addition or omission of ingredients or components of the item compared to its intended product specification, as well as misrepresentation or diversion of the packaged item from its intended course of sale. This leads to loss of potential revenue as counterfeit items are sold in the place of the real item. Also, there can be health or product related damages caused by not using an authentic item as opposed to a counterfeit—for example, the counterfeit can perform differently or not at all as compared to an authentic item. This is particularly acute in industries that can affect health and safety such as industries involved with pharmaceuticals, nutritional supplements, medical devices, food and beverages, construction, transportation, and defense.

As international criminal organizations become more sophisticated, existing packaging security is proving inadequate. The complexity of many industry supply chains—for example, the supply chain of the pharmaceutical industry—lends itself to entry points for adulterated or counterfeit product(s), often found in carefully counterfeited and high-quality packaging, and sometimes in authentic packaging that has either been stolen or as part of a repackaging operation.

In complex product supply chains and markets with variable pricing, opportunities for arbitrage exist for unscrupulous parties to misrepresent product pricing without any change to the underlying product, and thus benefit monetarily, for example, as in returns, rebate or charge-back fraud. Monetary gain or loss to either side of a transaction may also result from errors in record-keeping.

In addition to counterfeiting or product misrepresentation, items that appear physically identical or similar, for example certain nutritional supplements, may actually contain different ingredients or components, but because of similar appearance may be unintentionally packaged or labeled incorrectly. Even if the items are otherwise identical, they may have different properties associated with the particular lot or batch conditions; for example, pharmaceuticals that otherwise appear identical may have different expiration dates and be incorrectly labeled due to failures or limitations in quality assurance protocols to ascertain such differences.

For product development and research, it may be beneficial at times to study and authenticate performance of items that appear identical but are made differently to learn whether or how those differences affect an end use. At times, it is important in such studies—for example in clinically masked (or 'blind') studies leading to pharmaceutical development—to be able to confidently identify the underlying item without revealing the true identity to study participants. In the case of pharmaceutical development and clinical trials, item-level identity error may be introduced, for example, at the contract research organization that repackages the various product formulations into masked unit-doses. Much time, cost, and effort goes into statistical sampling and chemical analyses to verify the true identity of the unit-doses that are ultimately administered.

In the effort to attain positive health outcomes in a more cost-effective and timely manner, healthcare providers need to focus on the adherence to health regimens, not just the efficacy of specific drugs. Understanding when, where and how often medicine is prescribed by a doctor, accurately and timely dispensed from a pharmacy, received by a patient, and consumed by the patient is helpful in understanding and verifying the effectiveness of the overall health regimen. Recording and collecting the data for appropriate analysis and study while also being able to confirm the underlying identity of the medicine at each stage is important to the reliability of the information collected.

BRIEF DESCRIPTION OF THE DRAWINGS

Various embodiments of the invention are disclosed in the following detailed description and the accompanying drawings.

DETAILED DESCRIPTION

Figure 1:
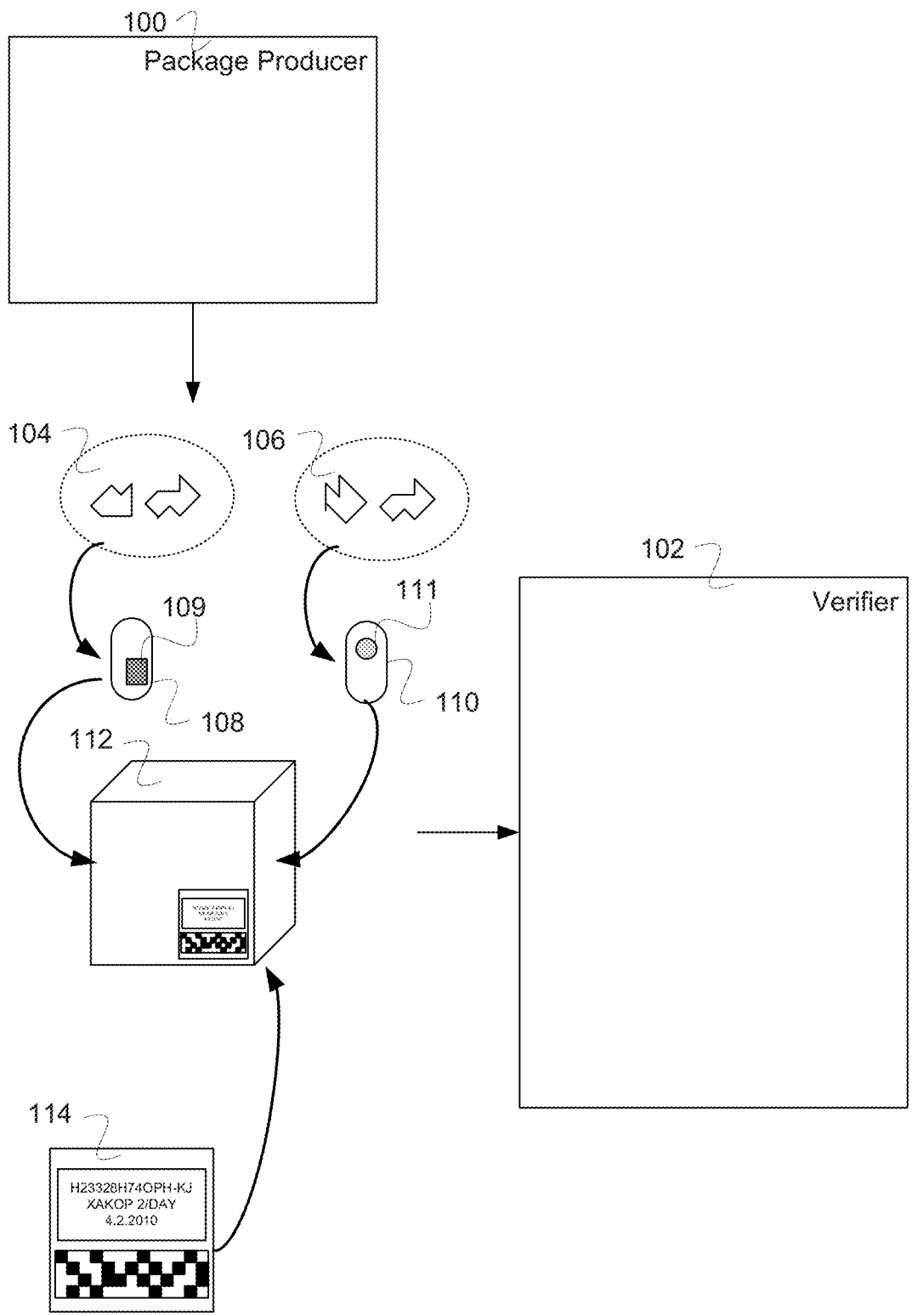
FIG. 1 is a block diagram illustrating an embodiment for a system for verifying an item in a package.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A system for verifying an item in a package is disclosed. The system comprises a package producer and a verifier. The package producer produces a package with a label. The package includes one or more items each with one or more selected tag identifiers that are placed in a location on the item. The verifier verifies the one or more items using 1) one or more selected tag identifiers as detected using a spectral measurement, 2) the location and/or shape of the tag identifiers on the item as detected using an imager, and 3) the label as read using a label reader.

In various embodiments, the label is comprised in part of information about the packaged items (hereby denoted goods information or goods info) that is useful to authenticate with the item. For example, goods info for medicines may contain dosage information, expiration dates, lot numbers, etc. Goods information may comprise different types of information depending on the associated item—for example, ingredient(s), stock keeping unit (SKU) number, identifier, physical characteristic (e.g., weight, dimension, volume, etc.), nutrition information, etc.

In various embodiments, the package contains individually identified items, the package contains one type of item identified with an identifier for the one type of item, or any other appropriate mapping of identifier(s) and/or item type, or any appropriate item or type of item. For example, each item (e.g., an individual art piece) has an individually identifiable set of tags or each type of item (e.g., all art pieces of a series of art pieces, a series of lithographic reproductions, etc.) has the same tag. So, that either each individual item is identifiable because it has a different tag, or all the items of the same type have the same tag so that the items of the type cannot individually be told apart but instead can be differentiated from other types of items (e.g., vitamin C tablets as opposed to vitamin D, or a low-dose type of medicine opposed to its higher-dose counterpart, etc.).

In various embodiments, the package comprises a pharmaceutical package that includes one or more solid oral dosage forms (SODFs: e.g., tablets, capsules, caplets, powders, crystals, and thin films, etc.), liquids (e.g., creams, gels, liniments, balms, lotions, injectables, and ointments, etc.), and/or any other appropriate medicines. The medicines have one or more added tag identifiers that are added into the outer coating, are distributed on the outer layer of an uncoated medicine (e.g., a SODF), are distributed throughout a SODF or liquid, or any other appropriate manner of adding a tag identifier. In some embodiments, each tag comprises a rugate filter. In some embodiments, the physical placement is used for identification—for example, the tags are laid out in a pattern (e.g., geometric shape, bar code, etc.) that is detectable using an imaging device. In some embodiments, the shapes of the tags are characterized and the characterization is used for identification.

In various embodiments, the package comprises a pharmaceutical package that includes one or more pills, liquids, test strips, transdermal patches or any other appropriate medicines or medical devices. The medicines have an added tag identifier that is added into the outer coating, is distributed on the outer layer of an uncoated medicine (e.g., a pill), is distributed throughout a pill or liquid, or any other appropriate manner of adding a tag identifier. In various embodiments, the package comprises an item—for example, an electronic chip, sub-component, medical devices, an automobile or airplane part, building or material supplies, clothing, toys, cosmetics, jewelry, watches, works of art, currency, tickets, official identification documents, wine, or gourmet food. In some embodiments, the tag comprises a rugate filter. In some embodiments, the physical placement is used for identification—for example, the tags are laid out in a shape (e.g., a circle, a square, etc.) or pattern (e.g., checkerboard, bar code, etc.) that is detectable using an imaging device. In some embodiments, the shape or shapes of one or more than one of the tags themselves are characterized and the characterization is used for identification. In some embodiments, individual tag placement is partially variable due to inclusion of a random or pseudorandom step in the tag placement process, allowing unique or nearly unique tag placement for each cluster of tags. In some embodiments, the verifier measures the location of one or more tags on an item or label, and from the tag locations and/or shapes produces a signature by means of an algorithm. In some embodiments, the algorithm uses the relative arrangement and/or shape of multiple tags with or without a fiduciary mark to produce a single item signature. In some embodiments, the algorithm produces a signature from the location and/or shape of each tag, and then combines the signatures from more than one tag on an item into a single signature. In some embodiments, the algorithm produces multiple signatures derived from the location and/or shape of one or more tags. In some embodiments, the verifier produces a single signature from the location and/or shape of one or more tags. For example, the use of a tag shape or combination of tag shapes, the placement of one or more tags in a pattern or arrangement or the relative locations of the one or more tags, or the spectral signature of a tag or of more than one tag are used alone or in combination to determine whether or not an item marked with the tag(s) is the authentic item.

In some embodiments, tags are made of the silica (deemed "generally recognized as safe"—or GRAS—by the FDA), rendering them biologically inert and edible. Each barely visible tag contains a custom-manufactured spectral signature chosen from over one billion possibilities, yet each item costs only fractions of a penny to label. The unique optical signature of each tag can be read by a low cost scanner and be linked to a label in a secure database, where additional information about the item can be stored, such as referencing a future e-pedigree track-and-trace system. Tags comprise a silicon wafer that is etched to have a spectral code encoded by the etching. The wafer is divided into small tags, and the resultant tags contain a complex porous nanostructure that is programmed during electrochemical synthesis to display a unique reflectivity spectrum. The tags are then oxidized by a high-temperature bake step to turn the crystalline, nanoporous silicon tags into amorphous, nanoporous silica. This bake step stabilizes the nanoporous structure against further oxidation (thus stabilizing the spectral signature) and provides for the tags to be characterized as a GRAS excipient. The spectrum is measured via a simple, low-cost spectrometer-based reader, then quickly verified against other information printed on the package, such that the medicine and packaging are authenticated together; tampering with either the package, or the contents, would flag a security violation. The tags can also be used on their own acting simply as labels for quality assurance or other purposes. Information capacity is projected to potentially reach one trillion possible unique spectra, using peak number, peak placement, peak rugate phase, and/or peak amplitude as modulation parameters. The tags are passive, inconspicuous and can be attached to the outside of medicines or food products to be read, for example, through clear or translucent plastic blister packs, or mixed into medicines or food as a forensic excipient, to be read as part of an investigation or inspection process by authorized security or quality assurance personnel.

In some embodiments, the tag properties comprise:
More than one billion codes available
Inconspicuous size range (20 μm to 150 μm) allows covert or semi-covert use
Made from clear, high purity silica rendering them biologically inert and edible
High temperature resistance—melting point above 1600° C.
Passive—no energy input or output
Can be used in or on a product, package, label, or security fiber
Can be applied via sprays, coatings, inks, varnishes, or as part of laminate
Can be integrated at a number of manufacturing stages
High level of security possible using random tag shapes; security can be scaled to suit specific product needs
Can be made self-authenticating and reduce the costs and security risks associated with online databases and maintenance
Each piece of the silica microtag contains the coded information, useful for forensics In some embodiments, a system verifying an item in a package comprises a package producer and a verifier. The package producer produces a package with a label, wherein the package includes an item each with one or more selected tag identifiers that are placed in a location on the item. The verifier verifies the item using 1) the one or more selected tag identifiers as detected using a spectral measurement or 2) a location or a shape of the one or more selected tag identifiers on the item, and 3) the label as read using a label reader. In various embodiments, the spectral measurement measures a number of a reflectance peak, an amplitude of a reflectance peak, a phase of a reflectance peak, or any other appropriate measurement. In some embodiments, the spectral measurement enables the decoding of a number. In some embodiments, the selected tag identifiers comprise silica. In various embodiments, the associated one or more selected tag identifiers are placed in a pattern, in a bar code, form a shape, or any other appropriate shape or location for an identifier.

In some embodiments, the package comprises one or more items, one or more selected tag identifiers, a package, and a label. Each item of the one or more items has an associated subset of identifiers of the one or more selected tag identifiers, wherein the subset of identifiers are placed in a location on one of the one or more items. The one or more items are placed in the package. The package includes the label, wherein 1) the label and 2) the location or shape of the one or more selected tag identifiers on the one or more items or the one or more selected tag identifiers as detected using a spectral measurement are used to verify the one or more items.

In some embodiments, the system for verifying a type of item in a package comprises a package producer and a verifier. The package producer produces a package with a label, wherein the package includes an item of the type each with an associated one or more selected tag identifiers that are placed in a location on the item. The verifier verifies the item using 1) placement information of the one or more selected tag identifiers on the item or 2) the associated one or more selected tag identifiers as detected using a spectral measurement, and 3) the label as read using a label reader. In various embodiments, the spectral measurement measures a number of a reflectance peak, an amplitude of a reflectance peak, a phase of a reflectance peak, or any other appropriate measurement. In some embodiments, the spectral measurement enables the decoding of a number. In some embodiments, the selected tag identifiers comprise silica. In various embodiments, the associated one or more selected tag identifiers are placed in a pattern, in a bar code, form a shape, or any other appropriate shape or location for an identifier.

FIG. 1 is a block diagram illustrating an embodiment for a system for verifying an item in a package. In the example shown, package producer 100 produces item 108 and item 110 each with associated tags (e.g., tags 104 and tags 106). Tags 104 are placed on item 108 in placement 109. Tags 106 are placed on item 110 in placement 111. In some embodiments, tags 104 and tags 106 are produced in a batch and selected for being associated with each item (e.g., item 108 and item 110). In some embodiments, tags are selected based on a tag shape or a characteristic of a tag shape (e.g., a roughness, a size, a shape, etc.). Items are placed in packaging 112 that includes label 114. In various embodiments, label 114 includes encoded information of one or more of the following: item type, item potency, item name, item stock keeping unit number, spectral response of the tag associated with the item, item shape, tag shape(s), tag placement information, item usage information, or any other appropriate information.

Verifier 102 also reads tags 104 and tags 106 using a spectral reader of verifier 102. Tag shape and/or tag placement is read using an imager of verifier 102. Verifier 102 verifies the authenticity of package 112 using information on label 114, spectral reading of tags, tag shape and/or tag placement information, or any other appropriate information. Linkages of the information in the label, information encoded in the tag, information encoded in the placement, are formed so that incorrect components are detected (e.g., any tampering or substitution is detected).

Figure 2:
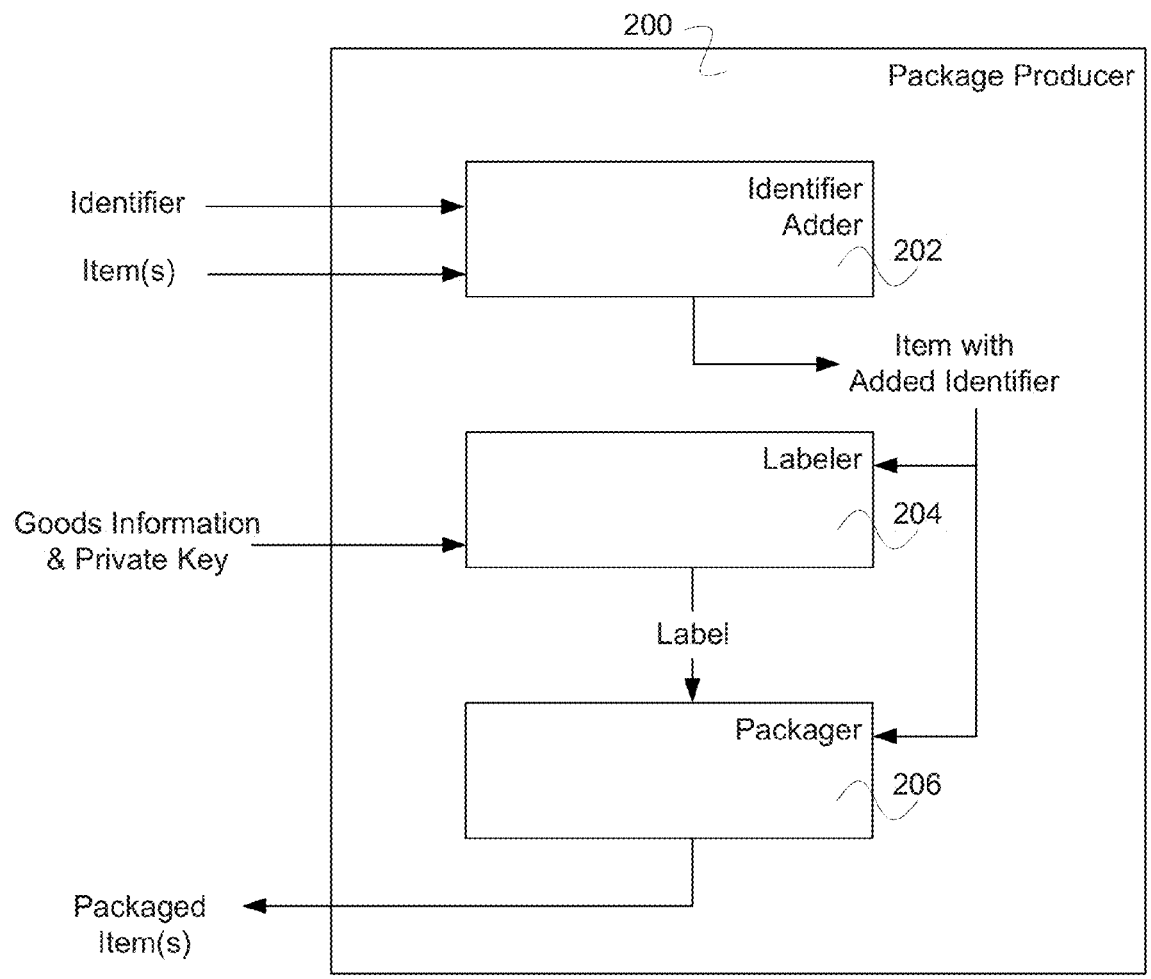
FIG. 2 is a block diagram illustrating an embodiment of a package producer.

FIG. 2 is a block diagram illustrating an embodiment of a package producer. In some embodiments, package producer 200 is used to implement package producer 100 of FIG. 1. In the example shown, package producer 200 comprises identifier adder 202, labeler 204, and packager 206. Identifier adder 202 receives an identifier (e.g., tag(s)) and item(s) and adds the identifier to the item(s). The item with identifier is measured by labeler 204 for spectral information from the tag, placement information of the tag on the item (e.g., in a pattern, in a code, forming a shape, etc.), and tag shape and/or characteristic information. Labeler 204, based on the information detected from the items and key and/or goods information, generates a label for a package for the item. Label is added to the package using packager 206.

Figure 3:
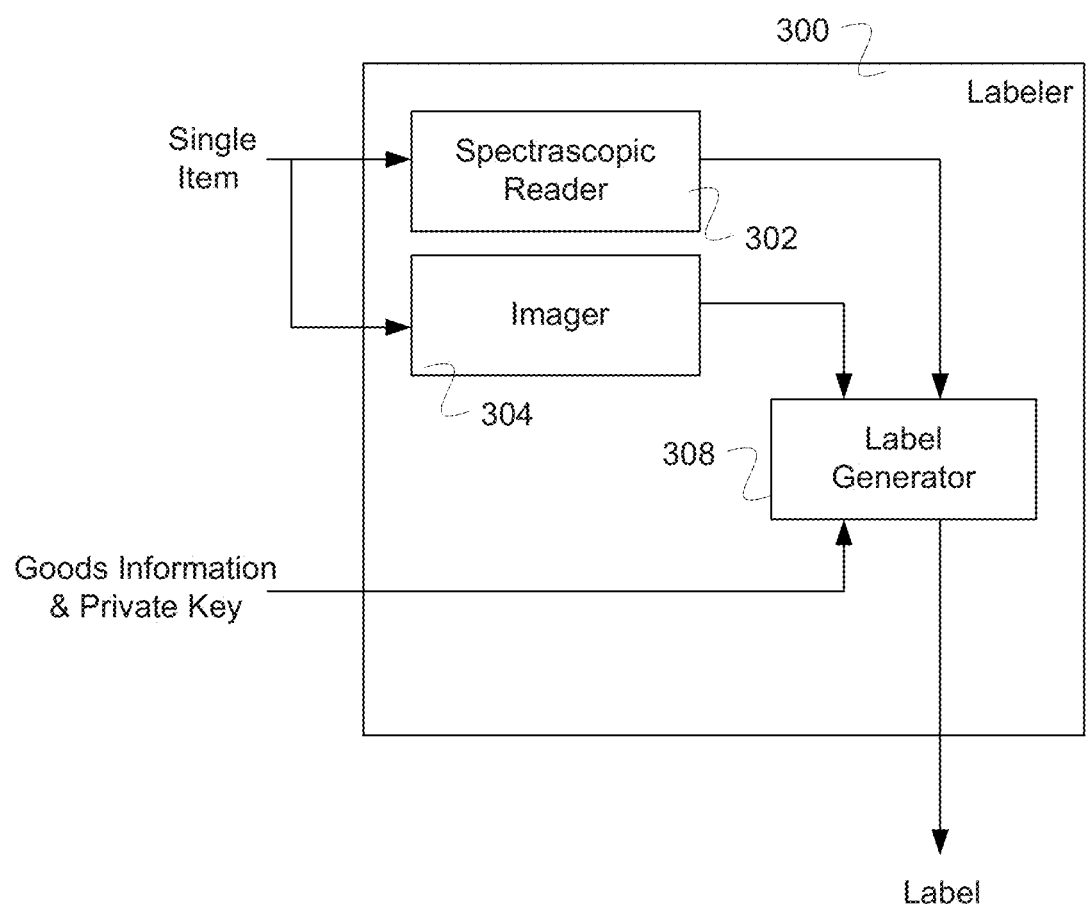
FIG. 3 is a block diagram illustrating an embodiment of a labeler.

FIG. 3 is a block diagram illustrating an embodiment of a labeler. In some embodiments, labeler 300 is used to implement labeler 204 of FIG. 2. In the example shown, labeler 300 comprises spectroscopic reader 302, imager 304, and label generator 308. Spectroscopic reader 302 reads one or more spectra from a tag or tags associated with an item. Imager 304 images an item and/or the placement of tags and/or the shape of tags. Information from spectroscopic reader 302 and imager 304 is input to label generator 308 along with goods information and a private key. For example, first spectroscopic reader 302 reads one or more tag spectra and outputs a number encoded in the reflectance spectra of the measured tags. By measuring certain spectral properties, such as the number, amplitude, phase, and/or positions of engineered reflectance peaks in each spectrum, the encoded number is derived (e.g., by using a predetermined mapping between the measured spectral properties and the encoded number).

Imager 304 captures an image of the marker and outputs a unique number related to the image. For example, by measuring the presence or absence of a tag in an inferred grid defined by printed fiduciary printed marks, creating a number from the grid by considering the presence of a tag as a 1 and the absence of a tag as 0, and concatenating each separate row in the grid into a single row, which can be seen as a binary number. The unique number is then combined with the reflectance-derived number, either by concatenation or another mathematical process, to create a unique marker ID. The marker ID is then combined with goods info (again by either concatenation or a more complex process) and the result digitally signed using the private key. The label then contains the computed digital signature, marker ID and goods info.

Figure 4:
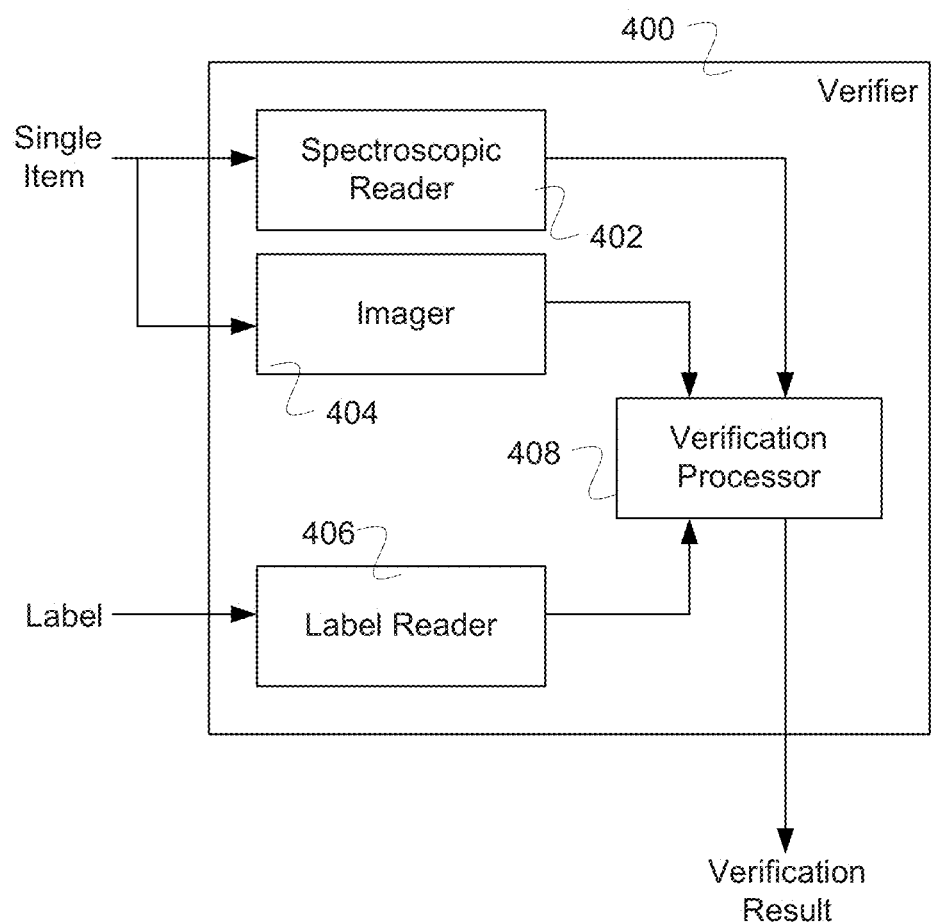
FIG. 4 is a block diagram illustrating an embodiment of a verifier.

FIG. 4 is a block diagram illustrating an embodiment of a verifier. In some embodiments, verifier 400 is used to implement verifier 102 of FIG. 1. In the example shown, verifier 400 comprises spectroscopic reader 402, imager 404, label reader 406, and verification processor 408. Spectroscopic reader 402 reads one or more tags associated with an item. Imager 404 images an item and/or the placement of tags and/or the shape of tags. Label reader 406 reads label from package. Information from spectroscopic reader 402 and imager 404 and label reader 406 is input to verification 408 along with goods information and a public key. The verification processor 408 verifies the digital signature using the public key of the public/private key pair. If the digital signature is deemed invalid, a verification failure is detected. Otherwise, the verification processor 408 uses the information from the spectroscopic reader 402 and imager 404 to compute the marker ID as described in the above description of FIG. 3. If the computed marker ID matches the marker ID read from the label to a sufficient degree defined by an acceptable reader error metric, the verification processor outputs a signal indicating successful verification.

Figure 5:
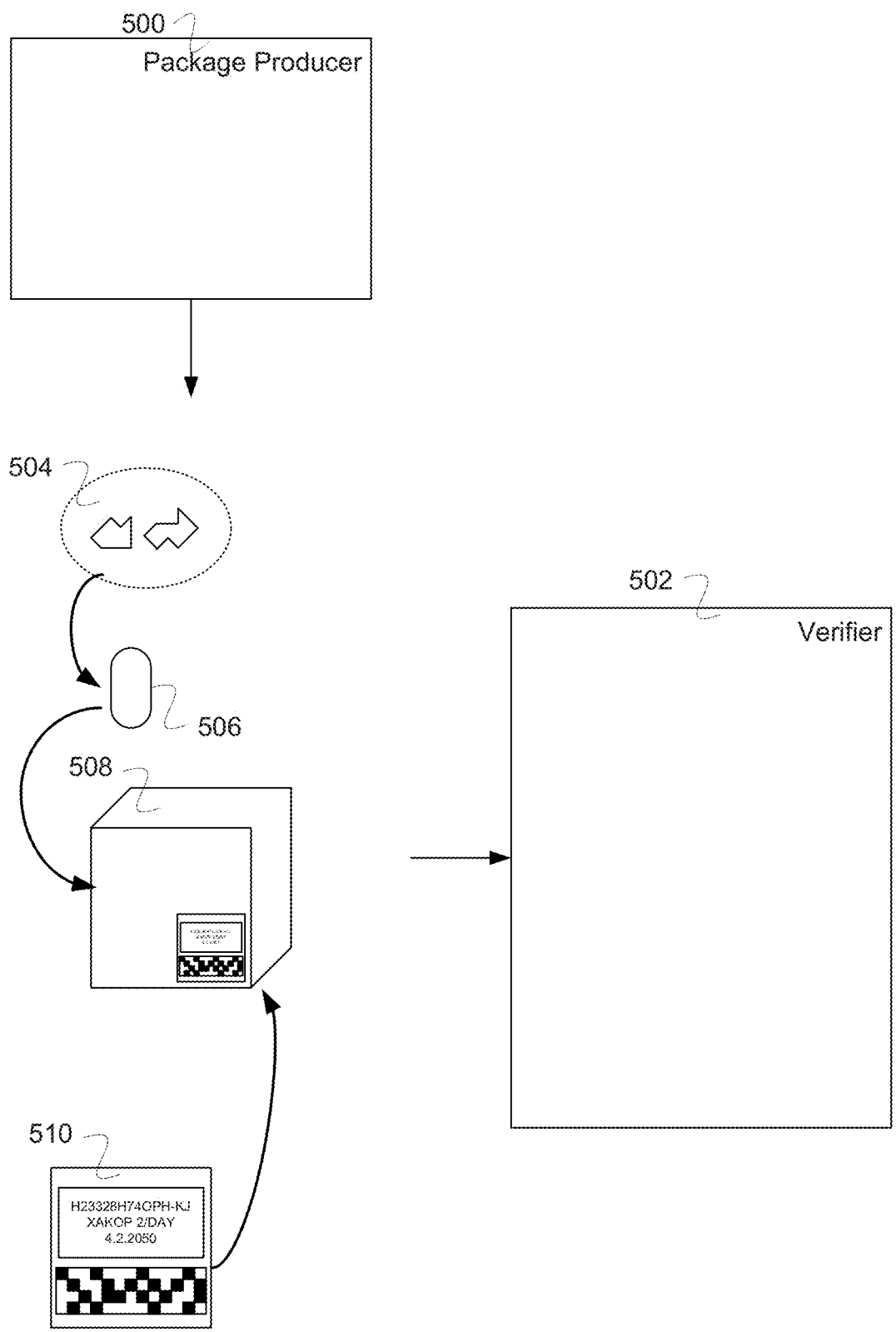
FIG. 5 is a block diagram illustrating an embodiment for a system for verifying an item in a package.

FIG. 5 is a block diagram illustrating an embodiment for a system for verifying an item in a package. In the example shown, package producer 500 produces item 506 with associated tags (e.g., tags 504). In some embodiments, tags 504 are produced in a batch and selected for being associated with all items (e.g., item 506). In some embodiments, tags are selected based on a tag shape or a characteristic of a tag shape (e.g., a roughness, a size, a shape, etc.). Items are placed in packaging 508 that includes label 510. In various embodiments, label 510 includes encoded information of one or more of the following: item type, item potency, item name, item stock keeping unit number, a spectral response of the tag associated with the item, item shape, tag shape(s), tag placement information, item usage information, or any other appropriate information.

Verifier 502 also reads tags 504 using a spectral reader of verifier 502. Tag shape and/or tag placement is read using an imager of verifier 502. Verifier 502 verifies the authenticity of package 508 using information on label 510, spectral reading of tags, tag shape and/or tag placement information, or any other appropriate information. Linkages of the information in the label, information encoded in the tag, information encoded in the placement, are formed so that incorrect components are detected (e.g., any tampering or substitution is detected).

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A package, comprising:
    one or more items;
    one or more selected tag identifiers, wherein each item of the one or more items has an associated subset of identifiers of the one or more selected tag identifiers, wherein the subset of identifiers are placed in a location on one of the one or more items, wherein each of the one or more selected tag identifiers comprises a silica tag with a unique optical signature; and
    wherein the one or more items are placed in the package; and
    a label, wherein the package includes the label, wherein the label and a reading of the subset of identifiers on the one or more items using a spectral measurement are used to verify the one or more items.

2. A package as in claim 1, wherein the subset of identifiers are laid out in a pattern.

3. A package as in claim 1, wherein the subset of identifiers are laid out in a bar code.

4. A package as in claim 1, wherein the subset of identifiers are laid out in a shape.

5. A package as in claim 1, wherein the spectral measurement measures a number of reflectance peaks.

6. A package as in claim 1, wherein the spectral measurement measures an amplitude of a reflectance peak.

7. A package as in claim 1, wherein the spectral measurement measures a phase of a reflectance peak.

8. A package as in claim 1, wherein the spectral measurement enables the decoding of the unique optical signature.

9. A package, comprising:
    an item of a type;
    one or more selected tag identifiers, wherein the item has an associated subset of identifiers of the one or more selected tag identifiers, wherein the associated subset of identifiers are placed in a location on the item; wherein each of the one or more selected tag identifiers comprises a silica tag with a unique optical signature; and
    wherein the item is placed in the package; and
    a label, wherein the package includes the label, wherein the label and a reading of the subset of identifiers on the item of the type using a spectral measurement are used to verify the item of the type.

10. A package as in claim 9, wherein the associated subset of identifiers is placed in a pattern.

11. A package as in claim 9, wherein the associated subset of identifiers is placed in a bar code.

12. A package as in claim 9, wherein the associated subset of identifiers form a shape.

13. A package as in claim 9, wherein the spectral measurement measures a number of reflectance peaks.

14. A package as in claim 9, wherein the spectral measurement measures an amplitude of a reflectance peak.

15. A package as in claim 9, wherein the spectral measurement measures a phase of a reflectance peak.

16. A package as in claim 9, wherein the spectral measurement enables the decoding of the unique optical signature.

* * * * *